US00PP17057P3

(12) United States Plant Patent
Anderson et al.

(10) Patent No.: US PP17,057 P3
(45) Date of Patent: Aug. 22, 2006

(54) ***SCHEFFLERA* PLANT NAMED 'FAN'**

(50) Latin Name: *Schefflera arboricola*
Varietal Denomination: Fan

(76) Inventors: Eric T. Anderson, 20253 Elfin Forest Rd., Esc., CA (US) 92029; Peter Pittman, 29001 Southwest 209th Avenue, Homestead, FL (US) 33030

( * ) Notice: Subject to any disclaimer, the term of this patent is extended or adjusted under 35 U.S.C. 154(b) by 0 days.

(21) Appl. No.: 10/958,912

(22) Filed: Oct. 5, 2004

(65) Prior Publication Data

US 2006/0075536 P1 Apr. 6, 2006

(51) Int. Cl.
*A01H 5/00* (2006.01)

(52) U.S. Cl. ..... Plt./377

(58) Field of Classification Search ..... Plt./377
See application file for complete search history.

*Primary Examiner*—Kent Bell
*Assistant Examiner*—Louanne Krawczewicz Myers
(74) *Attorney, Agent, or Firm*—David B. Waller & Assoc.

(57) ABSTRACT

A distinct cultivar of *Schefflera arboricola* plant named 'Fan', characterized by its upright plant habit: rapid growth rate; closely-spaced leaves and parted palmate leaves that are palmately veined, very glossy and dark green which give a dense full appearance.

1 Drawing Sheet

Description: *Schefflera arboricola* 'Fan'.

Latin name and variety denomination: The present invention is a new and distinct cultivar of *Schefflera* plant, botanically known as, *Schefflera arboricola* and herein referred to by the name 'Fan'.

BACKGROUND OF THE INVENTION

The new cultivar was discovered by the inventors in a controlled environment in Homestead, Fla. United States in September 2003 as a naturally occurring mutation of *Schefflera arboricola.* The new cultivar was observed as a single plant in a group of plants of *Schefflera arboricola.* Compared to plants of *Schefflera arboricola,* the plants of the new *Schefflera* are denser having closely-spaced and parted palmate leaves that are palmately veined, very glossy and dark green.

Asexual propagation of the new cultivar by terminal cuttings taken in the controlled environment in Elfin Forest, Calif., United States, has shown that the unique features of this new *Schefflera* are stable and reproduced true to type in successive generations.

The new *Schefflera* has not been observed under all possible environmental conditions. The phenotype may vary somewhat with variations in environment such as temperature and light intensity, without, however, any variance in genotype. The following traits have been repeatedly observed and are determined to be the unique characteristics of plants of the new *Schefflera.* These characteristics in combination distinguish the new *Schefflera* as a new and distinct cultivar:

1. Upright plant habit.
2. Rapid growth rate.
3. Parted palmate leaves that are palmately veined and closely spaced.
4. Very glossy and dark green leaves.

BRIEF DESCRIPTION OF THE DRAWINGS

The accompanying color photographs illustrate the overall appearance of the new *Schefflera,* showing the colors as true as it is reasonably possible to obtain in color reproductions of this type.

DETAILED BOTANICAL DESCRIPTION

Figure 1:
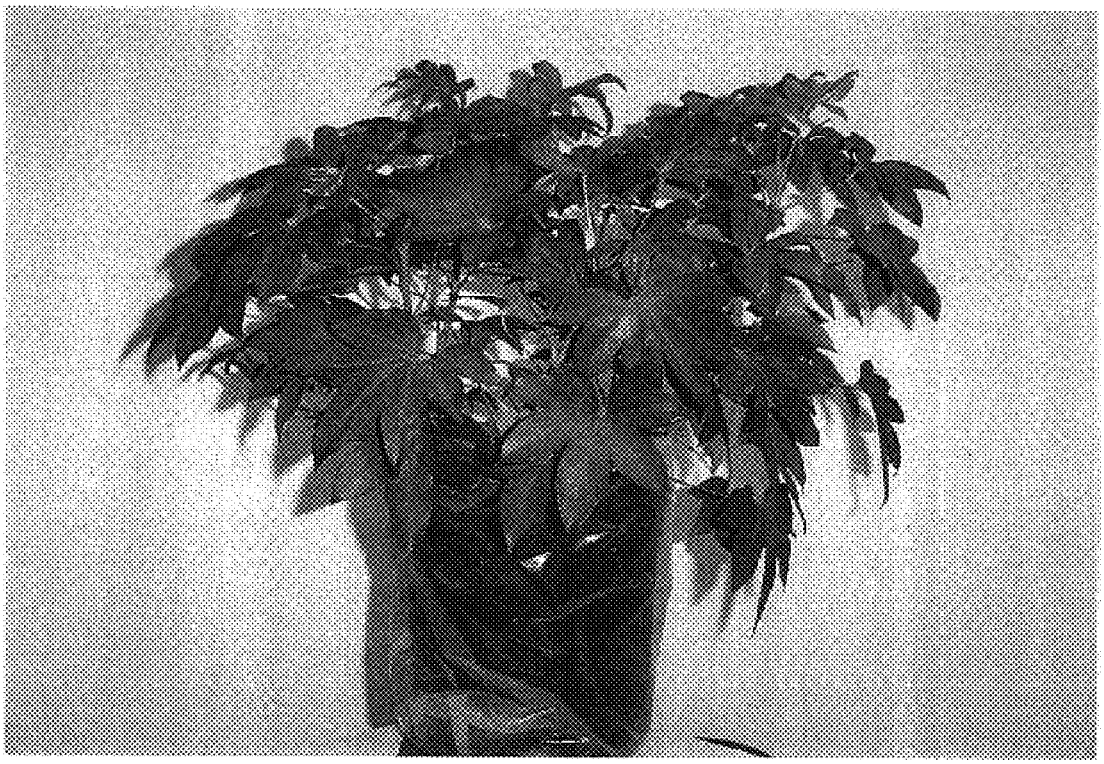
FIG. 1 is a photograph side perspective view of a typical potted plant of the new *Schefflera.*
Figure 2:
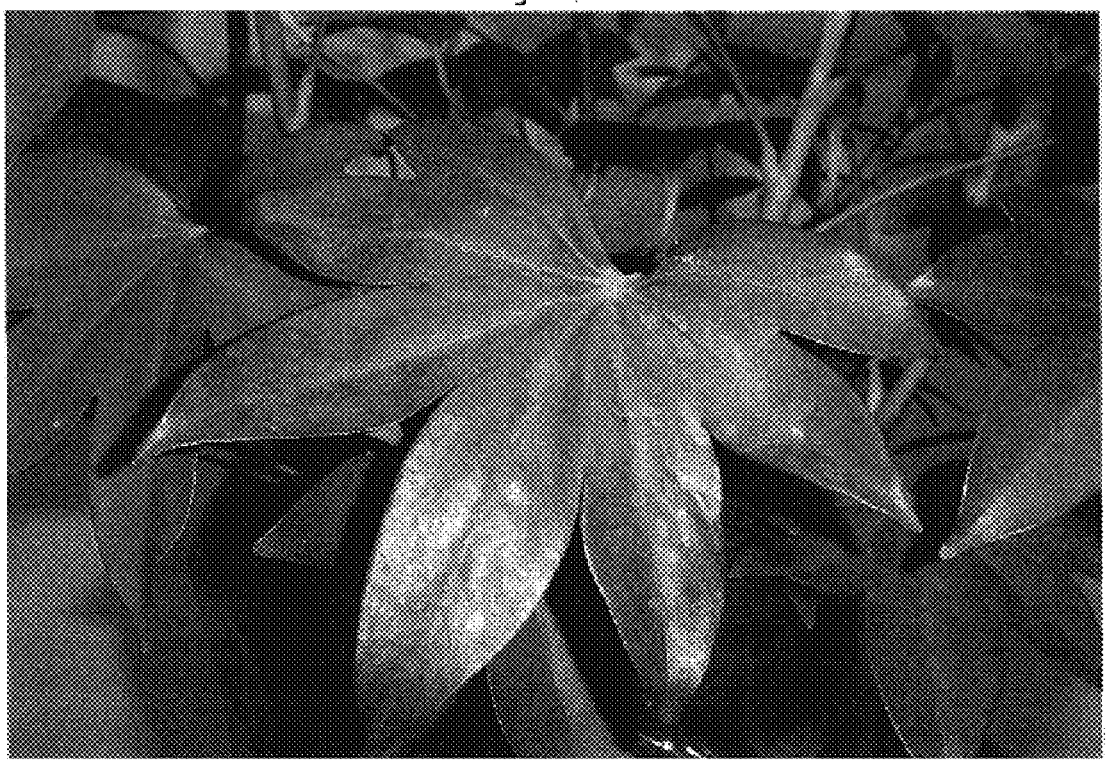
FIG. 2 is a close up photograph of a typical leaf of the new *Schefflera* plant. Leaf colors in the photograph may differ from the actual colors due to light reflectance.

In the following description, color references are made to The Royal Horticultural Society Colour Chart except where general terms of ordinary dictionary significance are used. Color designations are made for mature plants. The following observations and measurements describe four month old plants in 25 cm diameter containers grown in Elfin Forest, Calif., USA under commercial practice in a translucent plastic-covered greenhouse with day and night temperatures averaging 80° F. and 64° F. respectively. Average light level was 1,500 foot candles.

Botanical classification: *Schefflera arboricola* cultivar 'Fan'.

Parentage: The parent plant is unnamed *Schefflera arboricola* for which no patent has been identified (unpatented). The cultivar is a naturally occurring mutation of *Schefflera arboricola.*

Propagation type: By terminal cuttings.

Time to initiate roots: Winter: about 28 days at 70° F., Summer: About 21 days at 76° F.

Rooting habit: Numerous, fleshy and thick.

Plant description:

*Plant shape.*—Mostly erect and upright, inverted triangle, symmetrical.

*Growth habit.*—Bushy, dense and full.

*Plant type.*—Tropical evergreen tree.

*Plant height.*—About 300 to 400 cm from soil level to top of leaf plane.

*Plant diameter.*—About 100 cm.

*Plant vigor/crop time.*—High rapid growth rate under optimum temperature. Appropriate for 10 to 25 cm and larger containers. About 20 weeks are required to produce 100 cm tall plants.

Stem description/shape: Nearly round having an average diameter of about 8.0 mm to about 12.0 mm with internode length of about 2.5 to about 4.5 cm. Color: R.H.S. 144A. *Schefflera arboricola* "Fan" exhibits strong apical dominance and does not generally produce lateral branches.

Petioles: Average length about 15 cm having an average diameter of about 2.5 mm, color R.H.S. 144B.

Foliage description: Leaves: The leaves are arranged alternately on the stem with a single leaf per lateral stem. Shape: parted palmate having on average from 5 to 8 tips per leaf and are palmately veined. The average leaf varies on cultural conditions. Leaf length is from about 10.0 cm to about 13.0 cm. The leaf tip is cuspidate, the leaf base is sagittate-peltate and leaf margins are palmately lobed. Diameter: about 11 to about 16 cm. Texture: leathery, thick, smooth, very glossy, glabrous, and durable. Color: upper surface: glossy, dark green, R.H.S. 139A, Lower surface: R.H.S. 146A. Upper and lower surface venation: R.H.S. 145A.

Flower description: Flowers have not been observed on plants of the new *Schefflera*.

Disease/insect resistance: This *Schefflera* has no special disease resistance as compared with other *Schefflera*s observed to date on plants grown under commercial shadehouse and greenhouse conditions.

TABLE 1

Comparison with Parent Plant

| Foliage Description | *S. arboricola* | Cultivar |
|---|---|---|
| Leaf Shape: | Obovate, with Acuminate tip | Parted Palmate, with 5 to 8 tips on average |
| Average Leaf Diameter: | 7.0 to 10.0 cm | 11.0 to 16 cm |
| Leaflets: | 7 to 8 up to 15 | no Leaflets |
| Petiole Length: | 10.0 to 15.0 cm | 15 cm on average |
| Internode Length: | 2.0 to 3.0 cm | 2.5 to 4.5 cm |

It is claimed:

1. A new and distinct cultivar of *Schefflera arboricola* plant named 'Fan', as illustrated and described characterized particularly as to uniqueness of a single parted palmate leaf per lateral stem having on average 5 to 8 tips.

* * * * *